(12) United States Patent
Westfall

(10) Patent No.: US 8,076,143 B2
(45) Date of Patent: Dec. 13, 2011

(54) METHOD FOR DETERMINING QUALITY OF MILK AND PRESENCE OF MASTITIS

(76) Inventor: Geofrey J. Westfall, Brooklyn, CT (US)

( * ) Notice: Subject to any disclaimer, the term of this patent is extended or adjusted under 35 U.S.C. 154(b) by 2047 days.

(21) Appl. No.: 11/137,826

(22) Filed: May 25, 2005

(65) Prior Publication Data

US 2006/0280848 A1   Dec. 14, 2006

(51) Int. Cl.
*A01K 43/00* (2006.01)
(52) U.S. Cl. .......................................... 436/23; 426/231
(58) Field of Classification Search .................... 436/23; 426/231
See application file for complete search history.

(56) References Cited

U.S. PATENT DOCUMENTS

| 4,793,285 A | 12/1988 | Marshall |
| 5,664,521 A | 9/1997 | Simpson et al. |
| 6,161,502 A | 12/2000 | Simpson et al. |
| 6,649,403 B1 | 11/2003 | McDevitt et al. |

FOREIGN PATENT DOCUMENTS

| WO | WO 00/27183 | 5/2000 |
| WO | WO 2005/006849 A1 | 1/2005 |

OTHER PUBLICATIONS

Anderson et al., Lactation, Iowa State University Press, 1985, pp. 158-163.
Schroeder, J. W., "Bovine Mastitis and Milking Management", North Dakota State University Extension Service, Apr. 1997.
Wescor MAS-D-TEC mastitis detector product literature, 1999 (1 page).
Draminski mastitis detector product literature, Jan. 2004 (1 page).
Filteau, S. et al., "Breast milk immune factors in Bangladeshi women supplemented postpartum with retinol or β-carotene," *Am. J. Clin. Nutr.*, vol. 69, pp. 953-958 (1999).
Filteau, S. et al., "Milk cytokines and subclinical breast inflammation in Tanzanian women: effects of dietary red palm oil or sunflower oil supplementation," *Immunology*, vol. 97, pp. 595-600 (1999).
Gomo, E. et al., "Subclinical mastitis amount HIV-infected and uninfected Zimbabwean women participating in a multimicronutrient supplementation trial," *Transactions of the Royal Society of Tropical Medicine and Hygiene*, vol. 97, pp. 212-216 (2003).
Tallamy, P. et al., "Influence of Mastitis on Properties of Milk, V. Total and Free Concentrations of Major Minerals in Skimmilk," *Journal of Dairy Science*, vol. 53, No. 10, pp. 1386-1388 (1970).
Konrad., H., "Beitrag zur flammenphotometrischen natrium- und Kaliumbestimmung in Milch" Die Nahrung, vol. 13, No. 6, 1969, pp. 537-544.
EPO Examination Report dated Nov. 9, 2009 from corresponding EPO patent application 06 760 385.2-2204.

*Primary Examiner* — Christine T Mui
(74) *Attorney, Agent, or Firm* — Kagan Binder, PLLC

(57) ABSTRACT

Methods of determining the quality of milk due to the presence of mastitis, by monitoring the concentration of various ions, and ratios of those ions, in the milk. As the level of mastitic infection progresses, the concentrations of sodium and chloride ions increase and the concentrations of potassium and calcium ions decrease. A ratio of sodium to potassium is more sensitive to infection detection than either ion concentration alone. Similarly, sodium to calcium, chloride to potassium and chloride to calcium is more sensitive than any of the ions alone.

3 Claims, No Drawings

METHOD FOR DETERMINING QUALITY OF MILK AND PRESENCE OF MASTITIS

FIELD OF THE INVENTION

The present invention is directed to the detection of mastitis in milk producing animals. Specifically, the invention provides teat dip compositions and methods for application.

BACKGROUND

As a result of traditional selective breeding methods, milk production in dairy cows far exceeds the requirements of the newborn calf. Because of udder size, position, and anatomic configuration for rapid removal of large volumes of milk, the mammary glands of dairy cows are especially prone to injury and infection. In particular, mastitis, an infection of the mammary gland, is common in milking dairy cows, sheep, goats, and other milk-producing animals.

Clinically, mastitis typically produces heat, swelling, tenderness and possible deformation of the udder. Although the milk from a mastitic udder is generally safe for human consumption, a major concern is the cost to producers. Mastitis causes a decrease in the amount and quality of milk produced by the infected cow. With decreased quality, the price obtained for the milk likewise decreases. In some instances, depending on the level of infection, the milk is completely unsuitable. When this occurs, there are more white blood cells, also called somatic cells, secreted into the milk. Milk having a somatic cell count of over 750,000/ml is considered unsaleable in the U.S. Other countries have different acceptable levels of somatic cell count.

In most modern milking operations, the milk from all cows being milked at a facility is combined together for sale. Unfortunately, milk from one mastitic cow may sufficiently taint the quality of the entire volume of milk, and thus decrease the price obtained for the entire volume.

A common test for the presence of mastitic infection is the California Mastitis Test (CMT). This test, however, is a manual test that takes several minutes and is very subject to interpretation.

Electrical conductivity testing of the milk is also a common test used for the presence of mastitic infection. This method of mastitis detection has not, however, been reliable.

What is desired is a fast, cost efficient method for determining the presence, and extent, of any mastitis infection, prior to the milk from an infected cow being mixed with higher quality milk.

SUMMARY OF THE DISCLOSURE

The present invention relates to methods for determining the quality of milk due to the presence of mastitis, by monitoring the concentration of various ions in the milk. In accordance with the method of the present invention, the milk is tested for its concentration of sodium, chloride, potassium and/or calcium ions. As the level of mastitic infection progresses, the concentrations of sodium and chloride ions increase and the concentrations of potassium and calcium ions decrease.

To obtain a more sensitive indication of infection and decreased milk quality, ratios of sodium, chloride, potassium and/or calcium ions can be monitored. A ratio of sodium to potassium is more sensitive to infection detection than either ion concentration alone. Similarly, sodium to calcium, chloride to potassium and chloride to calcium is more sensitive than any of the ions alone.

In one particular aspect, the invention is directed to a method for testing quality of milk, the method including measuring the concentration of at least two of potassium ion, chloride ion, potassium ion, and calcium ion in a sample of un-homogenized and un-pasteurized whole milk. Then, calculating a ratio of at least one of sodium/potassium, sodium/calcium, chloride/potassium, and chloride/calcium, and determining the quality of the milk based on that ratio.

The milk quality can be based on having a sodium/potassium ratio less than 30, less than 20, less than 15, or less than 10. The milk quality can be based on having a sodium/calcium ratio less than 30 or less than 20. The milk quality can be based on having a chloride/potassium ratio less than 80 or less than 50. The milk quality can be based on having a chloride/calcium ratio less than 80 or less than 50.

In another particular aspect, the invention is directed to a method for testing quality of milk by comparing two samples. The two samples may be, for example: a sample from a healthy cow compared to a sample from a questionable cow; a sample from a first quarter of a cow's udder and a sample from a second quarter of the same udder; a milk sample from a cow and a milk sample from the previous milking of the same cow. The method includes measuring the concentration of at least two of potassium ion, chloride ion, potassium ion, and calcium ion in a first sample of un-homogenized and un-pasteurized whole milk. Then calculating a ratio of at least one of sodium/potassium, sodium/calcium, chloride/potassium, and chloride/calcium in that milk. The concentration of at least two of potassium ion, chloride ion, potassium ion, and calcium ion is measured in a second sample of un-homogenized and un-pasteurized whole milk. Then, a ratio of at least one of sodium/potassium, sodium/calcium, chloride/potassium, and chloride/calcium is calculated for that milk. The ratio of the first sample is compared to the ratio of the second sample to determine the differences in quality of the two milk samples. The sample with the higher ratio is the one having a greater amount of mastitic infection.

The milk quality can be based on having the sodium/potassium ratio from the second milk sample being no more than 20× than the sodium/potassium ratio from the first milk sample, or no more than 10×, or no more than 5×. The milk quality can be based on having the sodium/calcium ratio from the second milk sample being no more than 15× than the sodium/calcium ratio from the first milk sample. The milk quality can be based on having the chloride/potassium ratio from the second milk sample being no more than 10× than the chloride/potassium ratio from the first milk sample. The milk quality can be based on having the chloride/calcium ratio from the second milk sample being no more than 10× than the chloride/calcium ratio from the first milk sample.

These and other aspects of the invention are described below.

DETAILED DESCRIPTION OF THE PREFERRED EMBODIMENT

Before the inventive methods of testing are disclosed and described, it is to be understood that this invention is not limited to the particular examples, compositions or methods disclosed herein, and that materials and methods may vary somewhat. It is also to be understood that the terminology used herein is used for the purpose of describing particular embodiments only and is not intended to be limiting.

The methods of the present invention are suitable for use with milk from any milk producing mammals including, for example, cattle, sheep, goats, llamas, pigs, camels, etc. Because cattle are one of the most common milk-producing animals, the present invention is described with reference to dairy cattle. However, the invention should not be construed as being limited to use with cattle.

As briefly described above, the present invention is directed to a simple and efficient method for quantitative monitoring the level of mastitic infection in a cow, by testing her milk output. Whole milk, non-homogenized and non-pasteurized, is tested and the concentration of various ions in the milk is compared.

It has been found that as the level of mastitic infection progresses, the concentrations of sodium and chloride ions increase and the concentrations of potassium and calcium ions decrease. No specific concentration or level of sodium, chloride, potassium or calcium ions in the milk of a healthy cow has been determined to be a threshold level for "normal". Likewise, no specific concentration or level of sodium, chloride, potassium or calcium ions has been determined to be a threshold level for an "infected" cow. Rather, the level of ions is related to the amount of infection present, and "normal" cows fall on one end of the range and "infected" cows fall on the opposite end of the range.

In accordance with the method of the present invention, the milk is tested for its concentration of sodium, chloride, potassium and/or calcium ions. Although it is necessary that one only of those ions be monitored, it has been determined that in order to obtain a more sensitive indication of infection, ratios of the ions can be monitored. As mentioned above, as the level of mastitic infection progresses, the concentrations of sodium and chloride ions increase and the concentrations of potassium and calcium ions decrease. Thus, a ratio of sodium to potassium would be more sensitive to infection than either ion concentration alone. Similarly, sodium to calcium, chloride to potassium and chloride to calcium would be more sensitive than any of the ions alone. For all four ratios, as the difference between the concentrations increases, the level of infection increases.

As stated above, there has been no threshold determined as to when a cow has acceptable ion concentration levels and thus acceptable milk; however, generalities can be made, with respect to dairy cows.

For sodium/potassium ratio, a ratio of 30 or higher is determined to be an unacceptable level of mastitic infection. In some embodiments, a ratio of 20 or higher is unacceptable. In other embodiments, a ratio of 15 or higher is undesirable, and a ratio of 10 or higher may be undesirable in other embodiments.

For sodium/calcium ratio, a ratio of 30 or higher is determined to be an unacceptable level of mastitic infection. In some embodiments, a ratio of 20 or higher is unacceptable. In other embodiments, a ratio of 15 or higher is undesirable, and a ratio of 10 or higher may be undesirable in other embodiments.

For chloride/potassium ratio, a ratio of 80 or higher is determined to be an unacceptable level of mastitic infection. In some embodiments, a ratio of 50 or higher is unacceptable. In other embodiments, a ratio of 40 or higher is undesirable, and a ratio of 20 or higher may be undesirable in other embodiments.

For chloride/calcium ratio, a ratio of 80 or higher is determined to be an unacceptable level of mastitic infection. In some embodiments, a ratio of 50 or higher is unacceptable. In other embodiments, a ratio of 40 or higher is undesirable, and a ratio of 20 or higher may be undesirable in other embodiments.

The method of this invention can also be used to directly compare the concentration ratios between two samples of milk to determine the relative qualities of the milks and to determine which, if either, has a possible mastitic infection. For example, the milk from a known healthy cow that is producing "good" milk can be compared to a cow of questionable health. The milk from the first quarter of an udder can be compared to the second quarter, and optionally to the third quarter and even the fourth quarter of the udder, to determine if only a portion of the cow's udder is infected and the milk produced by that quarter tainted. Additionally, the method provides a simple way to track the history of a cow, by comparing a milk sample against the previous milking's sample.

For the sodium/potassium ratio, an increase of 20× or higher, from a second sample compared to a first sample, is considered to be an unacceptable level of mastitic infection. In some embodiments, an increase of 10× or higher is unacceptable. In other embodiments, an increase of 5× or higher is undesirable, and an increase of 3× or higher may be undesirable in other embodiments.

For the sodium/calcium ratio, an increase of 15× or higher, from a second sample compared to a first sample, is considered to be an unacceptable level of mastitic infection. In some embodiments, an increase of 8× or higher is unacceptable. In other embodiments, an increase of 5× or higher is undesirable, and an increase of 3× or higher may be undesirable in other embodiments.

For the chloride/potassium ratio, an increase of 10× or higher, from a second sample compared to a first sample, is considered to be an unacceptable level of mastitic infection. In some embodiments, an increase of 3× or higher is unacceptable. In other embodiments, an increase of 2.5× or higher is undesirable, and an increase of 2× or higher may be undesirable in other embodiments.

For the chloride/calcium ratio, an increase of 10× or higher, from a second sample compared to a first sample, is considered to be an unacceptable level of mastitic infection. In some embodiments, an increase of 3× or higher is unacceptable. In other embodiments, an increase of 2.5× or higher is undesirable, and an increase of 2× or higher may be undesirable in other embodiments.

It is to be understood that in some instances, one ion concentration or one ratio calculation may be not indicative of the infection level of a cow. See for example, Table 3 of the Examples section, where Cow 1 appears less infected than Cow 2, when reviewing the sodium/calcium and chloride/calcium ratios, but more infected than Cow 2 when reviewing the sodium/potassium and chloride/potassium ratios.

In accordance with the present invention, the milk can be tested sample by sample manually, with a hand held instrument such as a chemical sensor or electrode. Various sensors, electrodes and detectors are commercially available to monitor the ion concentrations. Ion selective electrodes or sensors are currently the preferred method for testing the ion concentrations, however, other methods for measuring ion concentration can be used. The sensor or electrode may be configured to detect the concentration of one or more of the desired ions. The concentration can be measured and recorded by the operator, and the desired ratio calculated and recorded. Depending on the technology available, one could use a computerized system configured to measure and calculate the desired ratio. With some testing equipment, it may be necessary to use an ionic strength adjuster to obtain proper and/or accurate readings.

This method of the invention, however, is particularly conducive to automation. In most dairy operations, manual milking of the udder by a person no longer occurs. Modern milking systems attach a hose or line to each teat, referred to as a short-milk tube, and apply a pulsatile vacuum to the teat so that the sphincter muscle is intermittently opened and closed to release the milk. The milk flows through the line to the holding tank, where it is co-mingled with the milk from all the other cows.

In accordance with the method of the invention, a sensor or electrode is installed in the milk line, such as in the short-milk tube, upstream of the holding tank. Depending on the specific sensor and set-up used, multiple sensors or electrodes may be used. As the milk is obtained from the udder and passes through the line, the milk is tested, in line, for possible unacceptable infection. If an unacceptably high level is measured, the milk can be diverted to a holding tank or disposed, thus not mixing potentially poor quality milk with the other milk. By having a sensor in the short-milk tube, one quarter can be isolated, if only one quarter is determined to be infected. This system could be designed to be completely automated, with computer controlled valves or solenoid switching among the milk lines, removing the questionable milk from the system.

The invention will be further described and illustrated in the examples that follow. The examples are illustrative of the invention and should not be construed as limiting the scope to their details. All parts, percentages, ratios, etc. are by weight unless otherwise specified.

EXAMPLES

Test 1

A milk sample was obtained from a healthy, non-infected dairy cow. About 5 hours after obtaining the sample, the un-homogenized milk was tested for concentration and percentage of various ions. The results are reported in Table 1 and Table 2, below.

A milk sample was obtained from a known, infected dairy cow. About 5 hours after obtaining the sample, the un-homogenized milk was tested for concentrations and percentage of various ions. The results are reported in Table 1 and Table 2, below.

TABLE 1

| Ion   | Healthy Cow | Infected Cow |
|-------|-------------|--------------|
| Na    | 0.029M      | 0.0956M      |
| Cl    | 0.175M      | 0.212M       |
| K     | 0.0135M     | 0.0052M      |
| Ca    | 0.012M      | 0.0055M      |
| Na/K  | 2.15        | 18.38        |
| Na/Ca | 2.42        | 17.38        |
| Cl/K  | 12.96       | 40.77        |
| Cl/Ca | 14.58       | 38.54        |

TABLE 2

| Ion   | Healthy Cow | Infected Cow |
|-------|-------------|--------------|
| Na    | 0.057%      | 0.105%       |
| Cl    | 0.091%      | 0.147%       |
| K     | 0.173%      | 0.157%       |
| Ca    | 0.12%       | 0.04%        |
| Na/K  | 0.329       | 0.669        |
| Na/Ca | 0.475       | 2.625        |
| Cl/K  | 0.526       | 0.936        |
| Cl/Ca | 0.758       | 3.675        |

Test 2

Milk samples were obtained from three dairy cows. The un-homogenized milk was tested for somatic cell count (SCC) and for the concentration of various ions. The results are reported in Table 3, below.

An SCC of 200,000-350,000/ml is average for dairy cows, a level of 100,000/ml or less is considered to be especially good milk, and a level of 750,000/ml is the legal limit for acceptable milk. Based on the SCC, the milk from Cow 1 and Cow 3 was unacceptable, and the milk from Cow 2 was close to the legal limit of being saleable in the U.S.

TABLE 3

|       | Cow 1     | Cow 2    | Cow 3     |
|-------|-----------|----------|-----------|
| SCC   | 2,000,000 | 700,000  | 2,000,000 |
| Na    | 0.00603M  | 0.00603M | 0.00657M  |
| Cl    | 0.0474M   | 0.0453M  | 0.0496M   |
| K     | 0.00560M  | 0.00593M | 0.00560M  |
| Ca    | 0.00230M  | 0.00189M | 0.00087M  |
| Na/K  | 1.07      | 1.02     | 1.17      |
| Na/Ca | 2.74      | 3.19     | 7.55      |
| Cl/K  | 8.46      | 7.64     | 8.86      |
| Cl/Ca | 20.61     | 23.97    | 57.01     |

From the foregoing detailed description and examples, it will be evident that modifications and variations can be made in the products and processes of the invention without departing from the spirit or scope of the invention. Therefore, it is intended that all modifications and verifications not departing from the spirit of the invention come within the scope of the claims and their equivalents.

I claim:

1. A method for testing quality of milk, the method comprising:
    (a) providing a sample of un-homogenized and un-pasteurized whole milk from a cow or a goat;
    (b) measuring the concentration of calcium ion, and sodium ion or chloride ion in the milk using no more than one ion selective electrode for each ion measured;
    (c) calculating either a ratio of the sodium/calcium or the chloride/calcium; and
    (d) determining whether the quality of the milk is acceptable based on the sodium/calcium ratio being less than 20 and the chloride/calcium ratio being less than 50.

2. A method for testing a relative quality of milk, the method comprising:
    (a) providing a first sample of un-homogenized and un-pasteurized whole milk from a cow or a goat;
    (b) measuring the concentration of the sodium ion and calcium ion in the first sample of milk using no more than one ion selective electrode for each ion measured;
    (c) calculating a ratio of the sodium/calcium in the first sample of milk;
    (d) providing a second sample of un-homogenized and un-pasteurized whole milk from a cow or a goat;
    (e) measuring the concentration of sodium ion and calcium ion in the second sample of milk;
    (f) calculating a ratio of the sodium/calcium in the second sample of milk; and
    (g) comparing the ratio from the first sample of milk to the second sample of milk to determine the relative quality of the first sample and the second sample, with the ratio from the second sample being no more than 15× than the ratio from the first sample.

3. A method for testing a relative quality of milk, the method comprising:
    (a) providing a first sample of un-homogenized and un-pasteurized whole milk from a cow or a goat;
    (b) measuring the concentration of the chloride ion and calcium ion in the first sample of milk using no more than one ion selective electrode for each ion measured;

(c) calculating a ratio of the chloride/calcium in the first sample of milk;
(d) providing a second sample of un-homogenized and un-pasteurized whole milk from a cow or a goat;
(e) measuring the concentration of chloride ion and calcium ion in the second sample of milk;
(f) calculating a ratio of the s chloride/calcium in the second sample of milk; and
(g) comparing the ratio from the first sample of milk to the second sample of milk to determine the relative quality of the first sample and the second sample, with the ratio from the second sample being no more than 10× than the ratio from the first sample.

* * * * *